(12) United States Patent
Cabiri

(10) Patent No.: US 9,259,532 B2
(45) Date of Patent: Feb. 16, 2016

(54) CARTRIDGE INTERFACE ASSEMBLY

(75) Inventor: Oz Cabiri, Macabim-Reut (IL)

(73) Assignee: Medimop Medical Projects Ltd., Ra'anana (IL)

( * ) Notice: Subject to any disclaimer, the term of this patent is extended or adjusted under 35 U.S.C. 154(b) by 635 days.

(21) Appl. No.: 13/521,181

(22) PCT Filed: Jan. 19, 2011

(86) PCT No.: PCT/US2011/021605
§ 371 (c)(1),
(2), (4) Date: Jul. 9, 2012

(87) PCT Pub. No.: WO2011/090956
PCT Pub. Date: Jul. 28, 2011

(65) Prior Publication Data
US 2013/0190691 A1 Jul. 25, 2013

Related U.S. Application Data

(63) Continuation-in-part of application No. 12/689,250, filed on Jan. 19, 2010, now Pat. No. 7,967,795.

(51) Int. Cl.
*A61M 1/00* (2006.01)
*A61M 5/145* (2006.01)
*A61M 5/24* (2006.01)

(52) U.S. Cl.
CPC .......... *A61M 5/14566* (2013.01); *A61M 5/2425* (2013.01); *A61M 5/1456* (2013.01)

(58) Field of Classification Search
CPC .......... A61M 5/2425; A61M 5/14566; A61M 5/1456
USPC ........................................ 604/151, 209–211
See application file for complete search history.

(56) References Cited

U.S. PATENT DOCUMENTS

| 1,795,630 | A | | 3/1931 | Wilson |
| 2,860,635 | A | * | 11/1958 | Wilburn .................. 604/190 |
| 3,203,269 | A | | 8/1965 | Perrine |
| 3,212,685 | A | | 10/1965 | Swan et al. |

(Continued)

FOREIGN PATENT DOCUMENTS

| CN | 1747683 A | 3/2006 |
| CN | 1863566 A | 11/2006 |

(Continued)

OTHER PUBLICATIONS

U.S. Appl. No. 13/472,112 by Cabiri, filed May 15, 2012.

(Continued)

*Primary Examiner* — Edelmira Bosques
(74) *Attorney, Agent, or Firm* — Panitch Schwarze Belisario & Nadel LLP

(57) ABSTRACT

A cartridge interface assembly (80) characterized by a driving plunger (82) including an outer shaft (84), and a driver (86) including an inner shaft (88) movable telescopically with respect to the outer shaft (84), wherein rotation of the driver (86) causes the driving plunger (82) to advance in a direction away from the driver (86), and wherein the cartridge interface assembly (80) is inserted in a cartridge (22) in which a plunger (24) is slidingly disposed, and rotation of the driver (86) causes the driving plunger (82) to advance distally in the cartridge (22) until abutting against the plunger (24).

7 Claims, 5 Drawing Sheets

(56) References Cited

U.S. PATENT DOCUMENTS

| | | | |
|---|---|---|---|
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A | 4/1990 | Slate et al. |
| 4,929,241 A | 5/1990 | Kulli |
| 4,950,246 A | 8/1990 | Muller |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A | 11/1997 | Smith et al. |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Gregory et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,066,909 B1 | 6/2006 | Peter et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |

(56) References Cited

U.S. PATENT DOCUMENTS

| | | |
|---|---|---|
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 9,061,104 B2 | 6/2015 | Daniel |
| 9,061,110 B2 | 6/2015 | Avery et al. |
| 9,072,827 B2 | 7/2015 | Cabiri |
| 9,089,475 B2 | 7/2015 | Fangrow |
| 9,089,641 B2 | 7/2015 | Kavazov |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |

(56) References Cited

U.S. PATENT DOCUMENTS

| | | |
|---|---|---|
| 2002/0161332 A1 | 10/2002 | Ramey |
| 2002/0169215 A1 | 11/2002 | Meng |
| 2003/0009133 A1 | 1/2003 | Ramey |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2004/0010207 A1 | 1/2004 | Flaherty et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0260233 A1 | 12/2004 | Garibotto et al. |
| 2005/0033234 A1 | 2/2005 | Sadowski et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | DiIanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0185449 A1 | 8/2007 | Mernoe |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |

(56) References Cited

U.S. PATENT DOCUMENTS

| | | |
|---|---|---|
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | | |
|---|---|---|---|
| CN | 101090749 A | | 12/2007 |
| CN | 201941304 U | | 8/2011 |
| CN | 102186733 A | | 9/2011 |
| DE | 1064693 B | | 9/1959 |
| DE | 19717107 A1 | | 11/1998 |
| EP | 0017412 A1 | | 10/1980 |
| EP | 0222656 A1 | | 5/1987 |
| EP | 0401179 A1 | | 12/1990 |
| EP | 1530979 A1 | | 5/2005 |
| EP | 1666080 A1 | | 6/2006 |
| EP | 2060606 A1 | | 5/2009 |
| EP | 2498589 A1 | | 9/2012 |
| JP | H07-194701 A | | 8/1995 |
| JP | H09-505758 A | | 6/1997 |
| JP | 2001-512992 A | | 8/2001 |
| JP | 2002-505601 A | | 2/2002 |
| JP | 2002-507459 A | | 3/2002 |
| JP | 2002-528676 A | | 9/2002 |
| JP | 2003-501157 A | | 1/2003 |
| JP | 2003-527138 A | | 9/2003 |
| JP | 2003-534061 A | | 11/2003 |
| JP | 2004-501721 A | | 1/2004 |
| JP | 2004-512100 A | | 4/2004 |
| JP | 2005-523127 A | | 8/2005 |
| JP | 2005-270629 A | | 10/2005 |
| JP | 2007-509661 A | | 4/2007 |
| JP | 2008-534131 A | | 8/2008 |
| JP | 2008-220961 A | | 9/2008 |
| JP | 2009-502273 A | | 1/2009 |
| WO | 9009202 A1 | | 8/1990 |
| WO | 9307922 A1 | | 4/1993 |
| WO | 9407553 A1 | | 4/1994 |
| WO | 9513838 A1 | | 5/1995 |
| WO | 9609083 A1 | | 3/1996 |
| WO | 9632975 A1 | | 10/1996 |
| WO | 9700091 A1 | | 1/1997 |
| WO | 9710012 A1 | | 3/1997 |
| WO | 9733638 A1 | | 9/1997 |
| WO | 9857683 A1 | | 12/1998 |
| WO | 9929151 A1 | | 6/1999 |
| WO | 9959665 A1 | | 11/1999 |
| WO | 0025844 A1 | | 5/2000 |
| WO | 0187384 A1 | | 11/2001 |
| WO | 0189607 A2 | | 11/2001 |
| WO | 0189613 A1 | | 11/2001 |
| WO | 0202165 A2 | | 1/2002 |
| WO | 0234315 A1 | | 5/2002 |
| WO | 02072182 A1 | | 9/2002 |
| WO | 03090833 A1 | | 11/2003 |
| WO | 2004032990 A2 | | 4/2004 |
| WO | 2004105841 A1 | | 12/2004 |
| WO | 2005018703 A2 | | 3/2005 |
| WO | 2005037350 A2 | | 4/2005 |
| WO | 2006037434 A1 | | 4/2006 |
| WO | 2006069380 A1 | | 6/2006 |
| WO | 2006102676 A1 | | 9/2006 |
| WO | 2006104806 A2 | | 10/2006 |
| WO | 2007051563 A1 | | 5/2007 |
| WO | 2007056504 A1 | | 5/2007 |
| WO | 2008001377 A2 | | 1/2008 |
| WO | 2008014908 A1 | | 2/2008 |
| WO | 2008057976 A2 | | 5/2008 |
| WO | 2008072229 A2 | | 6/2008 |
| WO | 2008076459 A1 | | 6/2008 |
| WO | 2008078318 A2 | | 7/2008 |
| WO | 2009044401 | | 4/2009 |
| WO | 2009046989 A2 | | 4/2009 |
| WO | 2009125398 A2 | | 10/2009 |
| WO | 2009144085 A2 | | 12/2009 |
| WO | 2010078227 A1 | | 7/2010 |
| WO | 2010078242 A1 | | 7/2010 |
| WO | 2011075105 A1 | | 6/2011 |
| WO | 2011090955 A1 | | 7/2011 |
| WO | 2011090956 A2 | | 7/2011 |
| WO | 2011156373 A1 | | 12/2011 |
| WO | 2012032411 A2 | | 3/2012 |
| WO | 2012160157 A1 | | 11/2012 |
| WO | 2014179774 A1 | | 11/2014 |

OTHER PUBLICATIONS

U.S. Appl. No. 13/429,840 by Cabiri, filed Mar. 26, 2012.
Int'l Preliminary Report on Patentability issued Aug. 2, 2012 in Int'l Application No. PCT/US2011/021604.
U.S. Appl. No. 14/258,661 by Cabiri, filed Apr. 22, 2014.
Int'l Search Report and Written Opinion issued Jan. 7, 2014 in Int'l Application No. PCT/US2013/065211.
Office Action issued May 23, 2014 in U.S. Appl. No. 13/472,112 by Cabiri.
Office Action issued Jun. 3, 2014 in JP Application No. 2010-527595.
Office Action issued Jul. 7, 2014 in U.S. Appl. No. 12/244,666 by Gross.

(56) References Cited

OTHER PUBLICATIONS

Int'l Search Report and Written Opinion issued Jul. 31, 2014 in Int'l Application No. PCT/US2014/033598.
Office Action issued Nov. 5, 2014 in U.S. Appl. No. 13/643,470 by Alon.
U.S. Appl. No. 14/553,399 by Cabiri, filed Nov. 25, 2014.
Office Action issued Nov. 2, 2014 in CN Application No. 201180006571.0.
Office Action issued Nov. 21, 2014 in U.S. Appl. No. 13/472,112 by Cabiri.
Office Action issued Nov. 21, 2014 in U.S. Appl. No. 131429,840 by Cabiri.
Int'l Preliminary Report on Patentability issued Nov. 27, 2014 in Int'l Application No. PCT/US2013/039465.
U.S. Appl. No. 13/643,470 by Alon, filed Oct. 25, 2012.
U.S. Appl. No. 13/733,516 by Cabiri, filed Jan. 3, 2013.
English translation of an Office Action issued Jan. 30, 2013 in CN Application No. 200880117084.X.
U.S. Appl. No. 14/193,692 by Gross, filed Feb. 28, 2014.
Office Action issued Feb. 4, 2014 in EP Application No. 11 707 942.6.
English translation of an Office Action issued Mar. 5, 2014 in CN Application No. 200880117084.X.
Int'l Search Report and Written Opinion issued Apr. 3, 2014 in Int'l Application No. PCT/US2013/078040.
Extended European Search Report issued Mar. 27, 2014 in EP Application No. 14154717.4.
Office Action issued Feb. 28, 2014 in CN Application No. 201180006571.0.
Extended European Search Report issued Aug. 7, 2014 in EP Application No. 1417477.4.
Office Action issued Aug. 6, 2014 in EP Application No. 11 707 942.6.
Office Action issued Sep. 2, 2014 in JP Application No. 2012-550069.
Office Action issued Sep. 2, 2014 in JP Application No. 2012-550068.
Office Action issued Aug. 26, 2014 in CN Application No. 201180006567.4.
Int'l Preliminary Report on Patentability issued Oct. 9, 2014 in Int'l Application No. PCT/US2013/033118.
Office Action issued Oct. 9, 2014 in U.S. Appl. No. 13/873,335.
Office Action issued Jan. 8, 2013 in JP Application No. 2010-527595.
Int'l Preliminary Report on Patentability issued Feb. 7, 2013 in Int'l Application No. PCT/US2011/021604.
Int'l Preliminary Report on Patentability issued Feb. 7, 2013 in Int'l Application No. PCT/US2011/021605.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
Int'l Search Report and Written Opinion issued Jul. 26, 2013 in Int'l Application No. PCT/US2012/039465.
Int'l Search Report and Written Opinion issued Aug. 5, 2013 in Int'l Application No. PCT/US2013/033118.
U.S. Appl. No. 13/964,651 by Gross, filed Aug. 12, 2013.
Office Action issued Aug. 15, 2013 in CN Application No. 200880117084.X.
Office Action issued Oct. 9, 2013 in IL Application No. 208634.
Office Action issued Nov. 5, 2013 in JP Application No. 2010-527595.
Office Action issued Sep. 29, 2013 in CN Application No. 201080040968.7.
Office Action issued Nov. 4, 2013 in EP Application No. 11 709 234.6.
U.S. Appl. No. 13/521,167 by Cabiri, filed Jul. 9, 2012.
Office Action issued May 16, 2012 in U.S. Appl. No. 12/615,828.
Office Action issued Jul. 2, 2012 in U.S. Appl. No. 13/272,555.
Office Action issued May 3, 2012 in CN Application No. 200880117084.X.
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312; Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.
Office Action issued Sep. 30, 2010 in U.S. Appl. No. 12/689,250.
Int'l Search Report issued Jan. 12, 2011 in Int'l Application No. PCT/US2010/048556; Written Opinion.
U.S. Appl. No. 60/997,459, filed Oct. 2, 2007.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
International Preliminary Report on Patentability issued on Jul. 5, 2011 in International Application No. PCT/US2009/069552; Written Opinion.
Office Action issued Jul. 13, 2011 in U.S. Appl. No. 12/559,563.
Int'l Preliminary Report on Patentability issued Sep. 1, 2011 in Int'l Application No. PCT/US2010/048556.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
Int'l Search Report issued Oct. 12, 2011 in Int'l Application No. PCT/US2011/021605.
Office Action issued Oct. 28, 2011 in U.S. Appl. No. 12/615,828.
Int'l Search Report issued Sep. 22, 2011 in Int'l Application No. PCT/IL11/00368; Written Opinion.
Int'l Preliminary Report on Patentability issued May 14, 2015 in Int'l Application No. PCT/US2013/065211.
Office Action issued May 7, 2015 in JP Application No. 2012-550069.
Office Action issued May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action issued May 1, 2015 in U.S. Appl. No. 14/638,525 by Filman.
Office Action issued Jun. 4, 2015 in U.S. Appl. No. 13/667,739 by Cabiri.
Office Action issued Dec. 17, 2013 in JP Application No. 2012-529808.
Office Action issued Dec. 10, 2013 in CN Application No. 201180006567.4.
Office Action issued Jan. 8, 2014 in U.S. Appl. No. 13/521,167 by Cabiri.
U.S. Appl. No. 29/479,307 by Norton, filed Jan. 14, 2014.
U.S. Appl. No. 14/593,051 by Gross, filed Jan. 9, 2015.
U.S. Appl. No. 14/683,193 by Cabiri, filed Apr. 10, 2015.
Office Action issued Feb. 24, 2015 in U.S. Appl. No. 14/258,661 by Cabiri.
U.S. Appl. No. 14/638,525 by Filman, filed Mar. 4, 2015.
Extended European Search Report issued Feb. 23, 2015 in EP Application No. 14166596.8.
Office Action issued Mar. 10, 2015 in U.S. Appl. No. 13/643,470 by Alon.
Office Action issued Mar. 10, 2015 in U.S. Appl. No. 12/244,666 by Gross.
Extended European Search Report issued Feb. 23, 2015 in EP Application No. 14166591.9.
Office Action issued Mar. 10, 2015 in CN Application No. 201180006567.4.
Office Action issued Mar. 31, 2015 in JP Application No. 2012-550068.
Webpage description of Daikyo Crystal Zenith® polymer, Manufactured by Daikyo Seiko, Ltd. (Jan. 6, 2009).
Webpage description of Copaxone®, Manufactured by Teva Pharmaceutical Industries Ltd. . (Jan. 6, 2009).

(56) References Cited

OTHER PUBLICATIONS

Office Action issued Aug. 13, 2015 in U.S. Appl. No. 14/553,399 by Cabiri.
Notice of Allowance issued Aug. 24, 2015 in U.S. Appl. No. 29/479,307 by Norton.
Office Action issued Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action issued Sep. 30, 2015 in U.S. Appl. No. 13/667,739 by Cabiri.
Office Action issued Sep. 18, 2015 in U.S. Appl. No. 13/874,085 by Cabiri.
Partial European Search Report issued Nov. 24, 2015 in EP Application No. 14166592.7.
Office Action issued Nov. 6, 2015 in U.S. Appl. No. 14/715,791 by Cabiri.

* cited by examiner

CARTRIDGE INTERFACE ASSEMBLY

CROSS-REFERENCE TO RELATED APPLICATION

This application is a section 371 of International Application No. PCT/US2011/021605, filed Jan. 19, 2011, which was published in the English language on Jul. 28, 2011 under International Publication No. WO 2011/090956 which is a continuation-in-part of U.S. application Ser. No. 12/689,250 filed Jan. 19, 2010, the disclosures of which are incorporated herein by reference.

FIELD OF THE INVENTION

The present invention generally relates to external drug pumps, and particularly to an assembly for pushing a drug from a cartridge, in which the assembly interfaces between an actuator, e.g., a motor, and a pushing device, e.g., a plunger in the cartridge.

BACKGROUND OF THE INVENTION

External drug pumps are typically used to deliver to patients substances which contain large molecules which cannot be digested when administered orally, such as insulin. Typically, the pump is adhered to the abdomen of the patient and delivers the substance to the patient via a cannula or needle that is inserted into the patient's skin.

PCT Patent Application PCT/IL2008/001312 (published as WO 2009/044401) to Gross and Cabiri (as well as U.S. patent applications Ser. Nos. 12/244666 and 12/244668, the disclosures of which are incorporated herein by reference), describes an external drug pump. In this pump, a cartridge is provided that contains a substance to be administered to a subject. (The terms "drug" and "substance" are used interchangeably throughout the specification and claims, and encompass any material administered to a subject. The term "cartridge" throughout the specification and claims encompasses any container for a drug, such as but not limited to, a cartridge, vial, syringe, bottle, ampoule and many more, and is not limited to any size or shape.)

The cartridge is sealed by a stopper, and has first and second threaded elements (e.g., a screw and a nut) that are threadedly coupled to each other. The distal end of the second threaded element defines a coupling portion that couples the second threaded element to the stopper. The first threaded element is rotatable with respect to the cartridge, and is linearly immobile with respect to the cartridge during rotation of the first threaded element. The first threaded element, rotated by a motor, is configured to linearly advance the stopper and at least the distal end of the second threaded element toward the distal end of the cartridge, without substantially rotating the second threaded element and the stopper.

The following is provided to facilitate understanding of the above described assembly.

Reference is made to FIG. 1, which illustrates the relevant elements of the prior art cartridge assembly of WO 2009/044401 (based on FIG. 4 of that application), wherein a cartridge 22 is inserted into a housing base.

The distal end of cartridge 22 is inserted into a cartridge piercing mechanism 44, which pierces a seal at the distal end of cartridge 22 having a stopper 24 therein (the stopper being an example of a plunger, piston or pushing device; the stopper will also be referred to as a plunger). Cartridge 22 is then lowered into the housing base. Typically, opposing resilient arms 70 support the cartridge upon the housing base. As cartridge 22 is lowered into the housing base, a first cog 52 engages a second cog 54. (First cog 52 is rotated by the motor, not shown here.) In some applications, before insertion of cartridge 22 into the housing, first threaded element 26 protrudes a distance h from the proximal end of the cartridge. The proximal end of the first threaded element (or of second cog 54) comprises a rounded portion 74. Portion 34 of the housing base comprises an angled face 76. As rounded portion 74 slides past the angled face, the first threaded element is pushed the distance h inside the cartridge. As a result, the first and second threaded elements 26 and 28 and the stopper 24 are displaced towards the distal end of the cartridge 22. During operation, the motor (not shown) turns cog 52, which turns cog 54. This linearly advances stopper 24 towards the distal end of the cartridge 22, thereby administering the substance from cartridge 22.

Reference is now made to FIG. 2, which illustrates cartridge 22 with plunger 24 in an initial position before cartridge 22 has been filled. The cartridge is either pre-filled by the manufacturer or filled by the user, such as with a hypodermic needle 15 inserted through a septum 17 in cartridge 22 (FIG. 3) or through a septum 19 in the housing of the drug pump (FIG. 4). As shown in FIG. 3, the plunger 24 moves linearly in the cartridge 22 as the cartridge is filled. Because no two cartridges will be filled with exactly the same amount of substance, such as due to tolerances, different injected volumes, different diameters or other dimensions, different plunger shapes, air bubbles or other factors, there is unfortunately no definitive position of the plunger 24 after cartridge 22 has been filled. This can cause a problem because it is possible that the overall length of the geared and threaded mechanism (which is predefined) that interfaces with plunger 24 may not meet the filled position of plunger 24 (which is unknown), thereby causing a problem to properly push against plunger 24 in order to administer the substance.

SUMMARY OF THE INVENTION

The present invention seeks to provide an improved assembly for pushing a drug from a cartridge, in which the assembly interfaces between an actuator, e.g., a motor, and a pushing device, e.g., a plunger in the cartridge, as is described more in detail hereinbelow. The invention solves the above mentioned problem of the prior art. Although the invention is described with reference to PCT Patent Application WO 2009/044401, nevertheless it is understood that the invention is applicable for many types of motor-driven drug cartridges.

There is thus provided in accordance with an embodiment of the present invention a cartridge interface assembly including a driving plunger including an outer shaft, and a driver including an inner shaft movable telescopically with respect to the outer shaft, wherein rotation of the driver causes the driving plunger to advance in a direction away from the driver, and wherein the cartridge interface assembly is inserted in a cartridge in which a plunger is slidingly disposed, and rotation of the driver causes the driving plunger to advance distally in the cartridge until abutting against the plunger. The driver may include a gear wheel. The inner shaft may mate with an intermediate shaft, and the intermediate shaft may mate with the outer shaft, so that the shafts are movable telescopically with respect to one another.

In accordance with a non-limiting embodiment of the present invention the inner shaft is threadedly received inside a hollow portion of the intermediate shaft, and the intermediate shaft is threadedly received inside a hollow portion of the outer shaft.

There is also provided in accordance with an embodiment of the present invention a method for interfacing between a driver and a plunger slidingly disposed in a cartridge, the method including inserting a cartridge interface assembly in the cartridge, the cartridge interface assembly including a driving plunger including an outer shaft, and a driver including an inner shaft movable telescopically with respect to the outer shaft, and rotating the driver to cause the driving plunger to advance distally in the cartridge until abutting against the plunger.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
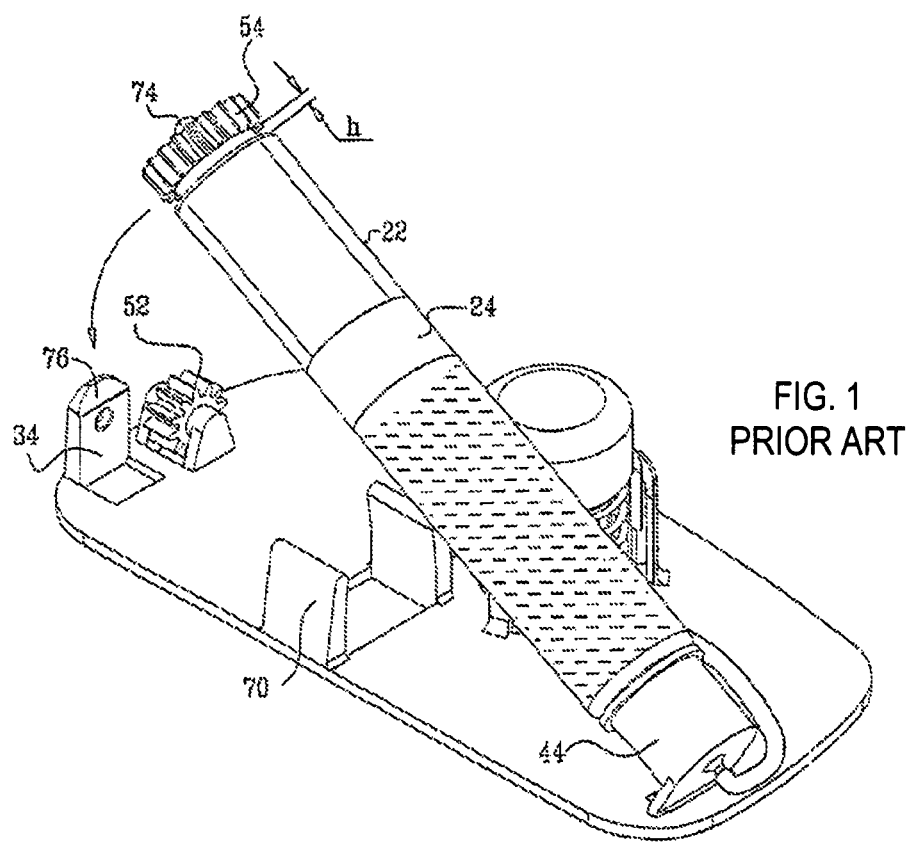
FIG. 1 is a simplified illustration of a prior art cartridge assembly.
Figure 2:
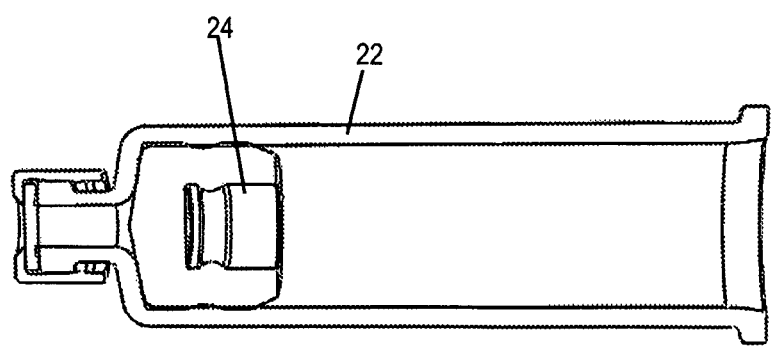
FIG. 2 is a simplified illustration of the prior art cartridge with plunger in an initial position before the cartridge has been filled.
Figure 3:
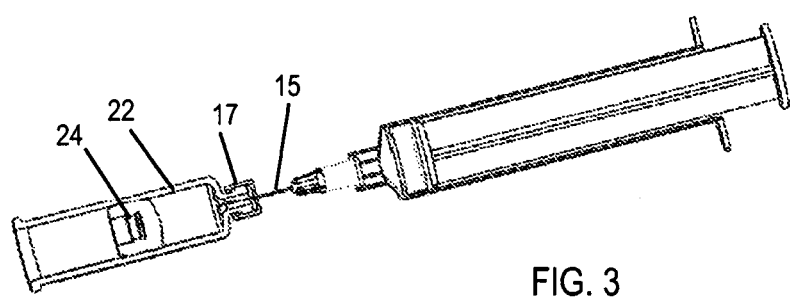
FIG. 3 is a simplified illustration of filling the prior art cartridge with a hypodermic needle inserted through a septum in the cartridge.
Figure 4:
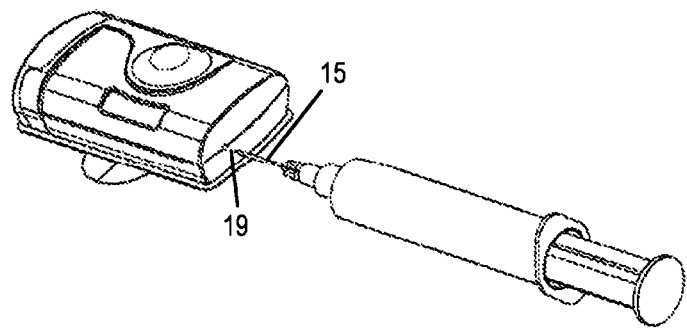
FIG. 4 is a simplified illustration of filling the prior art cartridge with a hypodermic needle inserted through a septum in a housing of a drug pump.
Figure 5:
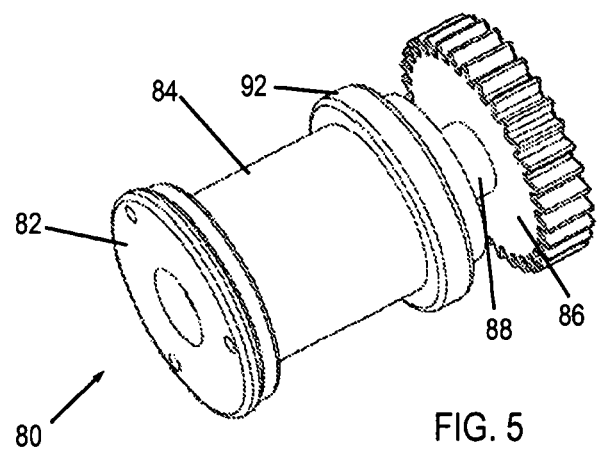
FIGS. 5 and 6 are simplified pictorial and sectional illustrations, respectively, of a cartridge interface assembly including a driving plunger, constructed and operative in accordance with an embodiment of the present invention.
Figure 6:
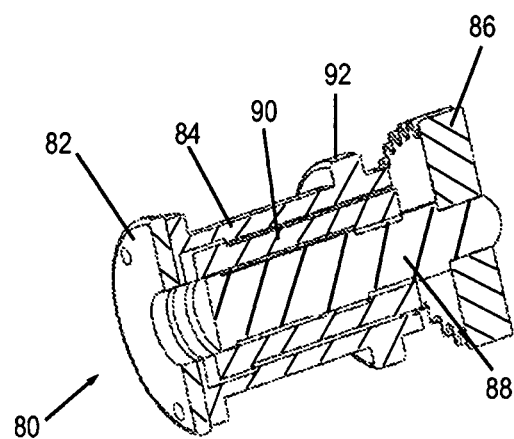

Reference is now made to FIGS. 5 and 6, which illustrate a cartridge interface assembly 80, constructed and operative in accordance with a non-limiting embodiment of the present invention.

Cartridge interface assembly 80 includes a driving plunger 82 at the distal end of an outer shaft 84. A driver 86, such as but not limited to, a gear wheel, includes an inner shaft 88. Inner shaft 88 is received inside a hollow portion of an intermediate shaft 90 and threadedly mates therewith. Intermediate shaft 90 is in turn received inside a hollow portion of outer shaft 84 and threadedly mates therewith. The shafts 84, 88 and 90 are arranged to move telescopically with respect to one another. Outer shaft 84 may further include a proximal O-ring 92. The driving plunger 82 and O-ring 92 are preferably made of an elastomer, such as natural or synthetic rubber. The other parts may be made of plastic or metal.

In an alternative embodiment, the intermediate shaft 90 may be omitted and inner shaft 88 and outer shaft 84 may be arranged to move telescopically with respect to one another. In further alternative embodiments, there may be more than three shafts arranged to move telescopically with respect to one another.

Figure 7:
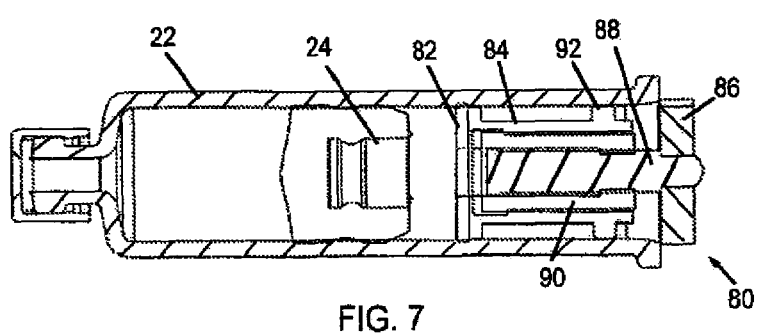
FIGS. 7 and 8 are simplified illustrations of the cartridge interface assembly inserted in a cartridge, respectively before and after the driving plunger abuts against the plunger of the cartridge, in accordance with an embodiment of the present invention.
Figure 8:
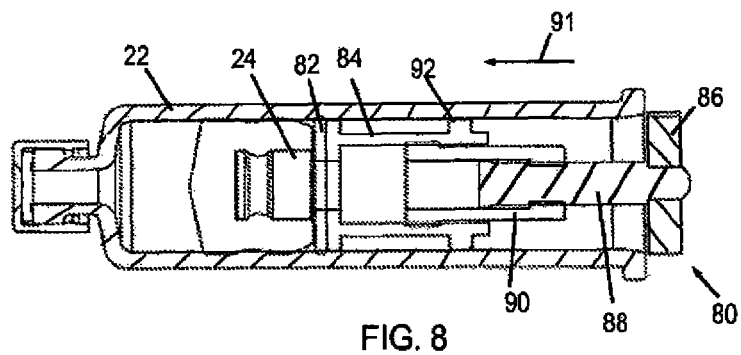

Reference is now made to FIG. 7, which illustrates the cartridge interface assembly 80 inserted in cartridge 22. Driving plunger 82 is initially distanced somewhat from plunger 24 of cartridge 22. Rotation of driver 86 (such as by meshing with a rotating motor not shown) causes inner shaft 88 to rotate, which causes intermediate shaft 90 to rotate and advance linearly towards the distal end of cartridge interface assembly 80, that is, in the direction towards driving plunger 82 as indicated by arrow 91. The distal movement of intermediate shaft 90 in turn causes outer shaft 84 to advance distally together with driving plunger 82. The friction of driving plunger 82 against the inner wall of cartridge 22 is such that it is much easier for driving plunger 82 to move linearly than to rotate, such that the rotation of inner shaft 88 and intermediate shaft 90 cause driving plunger 82 to advance distally in cartridge 22 until driving plunger 82 abuts against plunger 24 as shown in FIG. 8. In an alternative embodiment, driving plunger 82 is allowed to rotate somewhat as it advances linearly until it abuts against plunger 24. In another alternative embodiment, driving plunger 82 does not need to touch the inner wall of cartridge 22 and advances distally in cartridge 22 until it abuts against plunger 24.

Thus, with the present invention, no matter what the final position of plunger 24 is after filling cartridge 22 with the substance to be administered, the driving mechanism for pushing plunger 24 will always properly contact plunger 24 via cartridge interface assembly 80 due to the distance compensating action of cartridge interface assembly 80.

Figures 9, 10:
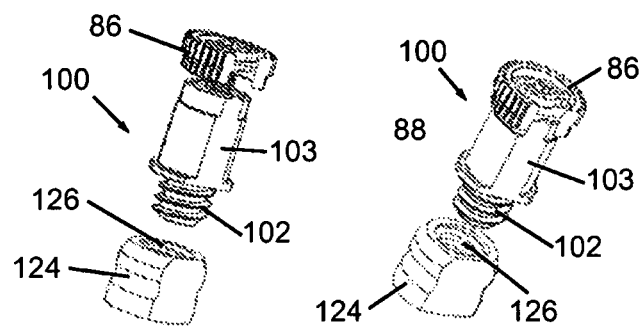
FIGS. 9 and 10 are simplified illustrations of a cartridge interface assembly, constructed and operative in accordance with another embodiment of the present invention, about to be screwed into a plunger of a cartridge, with the driver (gear wheel) moved away from, and abutting against, the body of the cartridge interface assembly, respectively.

Reference is now made to FIGS. 9 and 10, which illustrate an alternative embodiment of the cartridge interface assembly, with like elements being designated by like numerals. In this embodiment, a cartridge interface assembly 100 can be connected to a plunger 124 by a screw connection. The plunger 124 is formed with a threaded hole 126. The cartridge interface assembly 100 includes a threaded fastener 102 protruding from a distal end thereof, formed with male threads that correspond to the threaded hole 126. The threaded hole 126 and threaded fastener 102 are formed with right-hand (clockwise) threads. Accordingly, the telescoping shafts are formed with left-hand (counterclockwise) threads, so as to be opposite in direction to the threaded connection of the threaded fastener 102 into the threaded hole 126. The telescoping shafts of cartridge interface assembly 100 (such as the telescoping shafts 84, 88 and 90 of the first embodiment, not shown here) are rotated clockwise (as viewed from the distal end of driver 86) during operation in order to advance linearly towards the distal end of the cartridge interface assembly (as described above).

It may be desirable to supply the cartridge interface assembly 100 with the telescoping shafts fully inside a body 103 of the assembly 100 so that the driver 86 (shown in the illustrated embodiment of FIGS. 9 and 10 with a double gear wheel, but the invention is not limited to such a gear wheel) abuts against the proximal end of the body 103 of the cartridge interface assembly 100 as seen in FIG. 10. If the telescoping shafts are not turned tightly into the body to the position of FIG. 10, it may be possible for the shafts to unscrew during transportation and handling before assembly, with the result that the position of FIG. 10, which is the desirable position for assembly with the cartridge plunger, is not maintained. On the other hand, if the driver 86 is tightened too much against the body of assembly 100 in an effort to maintain the closed position of FIG. 10, this can increase the torque necessary for the motor to overcome the tight connection in order to start turning the driver 86, thereby overburdening the motor.

Figures 11A, 11B:
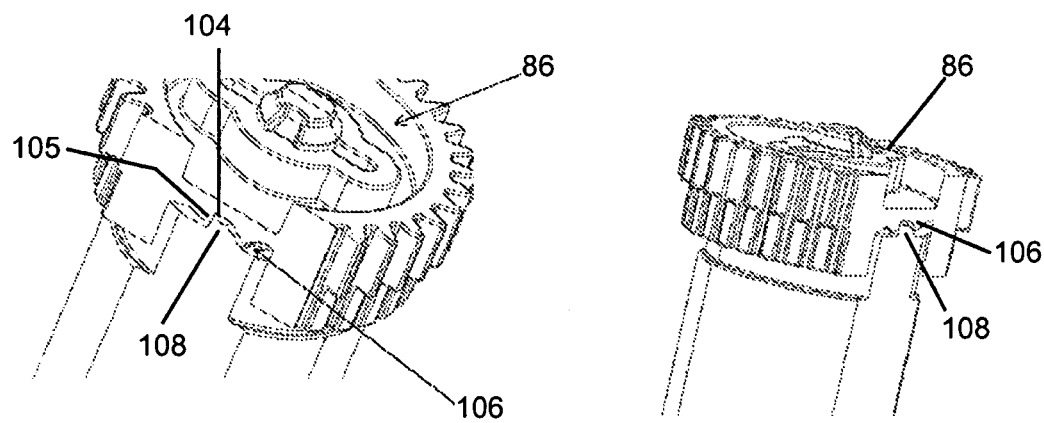
FIGS. 11A and 11B are close-up pictorial illustrations of the cartridge interface assembly of FIGS. 9 and 10, showing a locking assembly, constructed and operative in accordance with an embodiment of the present invention.

To solve this double problem (possible opening of telescoping shafts or the driver being tightened too much), a locking assembly is provided with the assembly 100 as is now described with reference to FIGS. 11A and 11B.

Driver 86 is formed with a recess 104, bounded by a wall 105 and a first locking tooth 106. The proximal end of the body 103 of the cartridge interface assembly 100 is formed with a second locking tooth 108. In the final position shown in FIGS. 11A and 11B (that of FIG. 10), second locking tooth 108 is received in recess 104. The first and second locking teeth 106 and 108 are formed with slanted walls 110 and 112, respectively. The slanted walls 110 and 112 can glide over each other in the clockwise direction, meaning that the second locking tooth 108 is free to move in and out of recess 104 in the clockwise direction. This permits rotation of driver 86 in the clockwise direction, which is the direction the motor turns driver 86 to advance the telescoping shafts distally. However, the second locking tooth 108 cannot move past wall 105, which means the second locking tooth 108 is cannot move past recess 104 in the counterclockwise direction, thereby preventing driver 86 from being unscrewed away from the proximal end of the body 103.

Thus the locking assembly of the first and second locking teeth 106 and 108 enables easy assembly of the telescoping shaft assembly with the plunger 124, and attains and maintains the final desired position of the driver 86 (i.e., the cartridge gear final position). The locking assembly prevents the telescoping shaft assembly from opening during transportation and handling, and ensures a small opening torque during operation.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A combination cartridge and cartridge interface assembly comprising:
   a rotationally immobile cartridge (22) having an inner cylindrical surface, a first stopper (24) slidingly inserted in the cartridge (22), a distal end and a substance therein for administration to a subject; and
   a cartridge interface assembly (80) comprising:
      a driving plunger (82) comprising a first shaft (84), the driving plunger (82) having an abutting surface and one or more outer surfaces in contact with the inner cylindrical surface of the cartridge (22);
      a driver (86) comprising a gear wheel and a second shaft (88) rotatably fixed to the gear wheel, said second shaft (88) mating with said first shaft (84), so that said shafts are movable telescopically with respect to one another, wherein rotation of said driver (86) causes said driving plunger (82) to linearly advance in a direction away from said driver (86), the arrangement being such that on insertion of the cartridge interface assembly (80) in the rotationally immobile cartridge (22), the one or more outer surfaces of the driving plunger (82) and the inner cylindrical surface of the cartridge (22) have a frictional relationship such that it is easier for the driving plunger (82) to move linearly than rotate within the cartridge, wherein the frictional relationship is the only force impeding rotation of the driving plunger (82) with respect to the cartridge (22) such that rotation of said driver (86) causes said driving plunger (82) to linearly advance only towards the distal end until the abutting surface of the driving plunger (82) abuts against the stopper (24) whereupon the driving plunger (82) urges the stopper (24) towards the distal end for metering substance from the cartridge; and
      a locking assembly that permits said driver (86) to rotate in a first rotational direction and blocks rotation of said driver (86) in a second rotational direction opposite to the first rotational direction.

2. The combination according to claim 1, wherein said second shaft (88) is threadedly received inside a hollow portion of said first shaft (84).

3. The combination according to claim 1, wherein said driving plunger (82) is at a distal end of said first shaft (84).

4. A combination cartridge and cartridge interface assembly comprising:
   a rotationally immobile cartridge (22) having an inner cylindrical surface, a first stopper (24) slidingly inserted in the cartridge (22), a distal end and a substance therein for administration to a subject: and
   a cartridge interface assembly (80) comprising:
      a driving plunger (82) comprising a first shaft (84), the driving plunger (82) having an abutting surface and one or more outer surfaces in contact with the inner cylindrical surface of the cartridge (22);
      a driver (86) comprising a second shaft (88). said second shaft (88) mating with said first shaft (84), so that said shafts are movable telescopically with respect to one another, wherein rotation of said driver (86) causes said driving plunger (82) to linearly advance in a direction away from said driver (86), the arrangement being such that on insertion of the cartridge interface assembly (80) in the rotationally immobile cartridge (22), the one or more outer surfaces of the driving plunger (82) and the inner cylindrical surface of the cartridge (22) have a frictional relationship such that it is easier for the driving plunger (82) to move linearly than rotate within the cartridge, wherein the frictional relationship is the only force impeding rotation of the driving plunger (82) with respect to the cartridge (22) such that rotation of said driver (86) causes said driving plunger (82) to linearly advance only towards the distal end until the abutting surface of the driving plunger (82) abuts against the stopper (24) whereupon the driving plunger (82) urges the stopper (24) towards the distal end for metering substance from the cartridge, an intermediate shaft (90) being threadedly received inside a hollow portion of said first shaft (84), said second shaft (88) being threadedly received inside a hollow portion of said intermediate shaft (90); and
      a locking assembly that permits said driver (86) to rotate in a first rotational direction and blocks rotation of said driver (86) in a second rotational direction opposite to the first rotational direction.

5. A combination cartridge and cartridge interface assembly comprising:
   a rotationally immobile cartridge (22) having an inner cylindrical surface, a first stopper (24) slidingly inserted in the cartridge (22), a distal end and a substance therein for administration to a subject; and
   a cartridge interface assembly (80) comprising:
      a driving plunger (82) comprising a first shaft (84), the driving plunger (82) having an abutting surface and one or more outer surfaces in contact with the inner cylindrical surface of the cartridge (22);

a driver (86) comprising a second shaft (88), said second shaft (88) mating with said first shaft (84), so that said shafts are movable telescopically with respect to one another, wherein rotation of said driver (86) causes said driving plunger (82) to linearly advance in a direction away from said driver (86), the arrangement being such that on insertion of the cartridge interface assembly (80) in the rotationally immobile cartridge (22), the one or more outer surfaces of the driving plunger (82) and the inner cylindrical surface of the cartridge (22) have a frictional relationship such that it is easier for the driving plunger (82) to move linearly than rotate within the cartridge, wherein the frictional relationship is the only force impeding rotation of the driving plunger (82) with respect to the cartridge (22) such that rotation of said driver (86) causes said driving plunger (82) to linearly advance only towards the distal end until the abutting surface of the driving plunger (82) abuts against the stopper (24) whereupon the driving plunger (82) urges the stopper (24) towards the distal end for metering substance from the cartridge, a threaded fastener (102) protrudes from a distal end of said cartridge interface assembly (100) that mates with a threaded hole (1 26) formed in said plunger (1 24); and a locking assembly that permits said driver (86) to rotate in a first rotational direction and blocks rotation of said driver (86) in a second rotational direction opposite to the first rotational direction.

6. A combination cartridge and cartridge interface assembly comprising:

a rotationally immobile cartridge (22) having an inner cylindrical surface, a first stopper (24) slidingly inserted in the cartridge (22), a distal end and a substance therein for administration to a subject; and a cartridge interface assembly (80) comprising:

a driving plunger (82) comprising a first shaft (84), the driving plunger (82) having an abutting surface and one or more outer surfaces in contact with the inner cylindrical surface of the cartridge (22);

a driver (86) comprising a second shaft (88), said second shaft (88) mating with said first shaft (84), so that said shafts are movable telescopically with respect to one another, wherein rotation of said driver (86) causes said driving plunger (82) to linearly advance in a direction away from said driver (86), the arrangement being such that on insertion of the cartridge interface assembly (80) in the rotationally immobile cartridge (22), the one or more outer surfaces of the driving plunger (82) and the inner cylindrical surface of the cartridge (22) have a frictional relationship such that it is easier for the driving plunger (82) to move linearly than rotate within the cartridge, wherein the frictional relationship is the only force impeding rotation of the driving plunger (82) with respect to the cartridge (22) such that rotation of said driver (86) causes said driving plunger (82) to linearly advance only towards the distal end until the abutting surface of the driving plunger (82) abuts against the stopper (24) whereupon the driving plunger (82) urges the stopper (24) towards the distal end for metering substance from the cartridge, said driver (86) being formed with a recess (104), bounded by a wall (105) and a first locking tooth (106), and a proximal end of a body (103) of said cartridge interface assembly (80, 100) is formed with a second locking tooth (108), which in a final assembly position, is received in said recess (104), and wherein said first and second locking teeth (106, 108) are formed with slanted walls (110, 112) which can glide over each other in the first rotational direction, but said second locking tooth (108) cannot move past said wall (105) in the second rotational direction.

7. A cartridge interface assembly (100), comprising:

a rotatable driver (86), linkable to a stopper (24), slidingly disposed in a cartridge (22) for advancing said stopper (24) distally in said cartridge for dispensing a substance from said cartridge (22), wherein a locking assembly permits said driver (86) to rotate in a first rotational direction and blocks rotation of said driver (86) in a second rotational direction opposite to the first rotational direction, wherein said driver (86) is formed with a recess (104), bounded by a wall (105) and a first locking tooth (106), and a proximal end of a body (103) of said cartridge interface assembly (100) is formed with a second locking tooth (108), which in a final assembly position, is received in said recess (104), and wherein said first and second locking teeth (106, 108) are formed with slanted walls (110, 112) which can glide over each other in the first rotational direction, but said second locking tooth (108) cannot move past said wall (105) in the second rotational direction.

* * * * *